United States Patent
Varshney et al.

(10) Patent No.: US 10,217,072 B2
(45) Date of Patent: Feb. 26, 2019

(54) ASSOCIATION-BASED PRODUCT DESIGN

(71) Applicant: INTERNATIONAL BUSINESS MACHINES CORPORATION, Armonk, NY (US)

(72) Inventors: Lav R. Varshney, Yorktown Heights, NY (US); Kush R. Varshney, Ossining, NY (US); Jun Wang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/976,350

(22) Filed: May 10, 2018

(65) Prior Publication Data

US 2018/0260750 A1    Sep. 13, 2018

Related U.S. Application Data

(63) Continuation of application No. 14/561,869, filed on Dec. 5, 2014, now Pat. No. 10,019,689.
(Continued)

(51) Int. Cl.
*G06F 19/00*    (2018.01)
*G06Q 10/06*   (2012.01)
(Continued)

(52) U.S. Cl.
CPC ...... *G06Q 10/0637* (2013.01); *A23L 3/34095* (2013.01); *A61L 2/16* (2013.01); *B01F 15/00318* (2013.01); *G01N 30/88* (2013.01); *G06F 17/11* (2013.01); *G06F 17/16* (2013.01); *G06F 17/3053* (2013.01); *G06F 17/30867* (2013.01); *G06F 17/30958* (2013.01);
(Continued)

(58) Field of Classification Search
None
See application file for complete search history.

(56) References Cited

U.S. PATENT DOCUMENTS 5,119,307 A * 6/1992 Blaha ............... G06F 17/50
                                                    700/107
5,311,424 A * 5/1994 Mukherjee ......... G06Q 10/06
                                                    700/105
(Continued)

OTHER PUBLICATIONS

Bae et al., "Product Development with Data Mining Techniques; A Case on design of Digital Camera," Expert Systems with Applications, vol. 38, No. 9, pp. 9274-9280, Aug. 2011.
(Continued)

*Primary Examiner* — Gurkanwaljit Singh
(74) *Attorney, Agent, or Firm* — Kurt Goudy

(57) ABSTRACT

A method for designing a new product includes automatically identifying a plurality of components of stored products, wherein the plurality of components is associated with an existing component included in a design of the new product, automatically selecting a new component from among the plurality of components, wherein a relationship between the existing component and the new component optimizes a design objective for the new product, automatically adding the new component to the design for the new product, and iteratively repeating the identifying, the selecting, and the adding until a stopping criterion is met, wherein the design for the new product is complete when the stopping criterion is met.

20 Claims, 6 Drawing Sheets

Related U.S. Application Data

(60) Provisional application No. 61/913,703, filed on Dec. 9, 2013.

(51) Int. Cl.

| | | |
|---|---|---|
| A61L 2/16 | (2006.01) | |
| A23L 3/3409 | (2006.01) | |
| G06Q 10/10 | (2012.01) | |
| G06Q 50/12 | (2012.01) | |
| G06F 17/50 | (2006.01) | |
| G06F 17/30 | (2006.01) | |
| B01F 15/00 | (2006.01) | |
| G01N 30/88 | (2006.01) | |
| G06F 17/11 | (2006.01) | |
| G06F 17/16 | (2006.01) | |
| G16H 20/60 | (2018.01) | |
| G16H 10/20 | (2018.01) | |
| G09B 19/00 | (2006.01) | |
| G01N 30/02 | (2006.01) | |

(52) U.S. Cl.
CPC .......... G06F 17/50 (2013.01); G06F 19/3475 (2013.01); G06Q 10/063 (2013.01); G06Q 10/1097 (2013.01); G06Q 50/12 (2013.01); G16H 10/20 (2018.01); G16H 20/60 (2018.01); *A23V 2002/00* (2013.01); *B01D 2257/90* (2013.01); *G01N 2030/025* (2013.01); *G01N 2030/8809* (2013.01); *G09B 19/0092* (2013.01)

(56) References Cited

U.S. PATENT DOCUMENTS

| | | | | |
|---|---|---|---|---|
| 5,630,070 A * | 5/1997 | Dietrich | G06Q 10/06 | 705/7.23 |
| 5,960,414 A * | 9/1999 | Rand | G06Q 10/06 | 705/22 |
| 6,003,012 A * | 12/1999 | Nick | G06F 17/50 | 700/95 |
| 6,009,406 A * | 12/1999 | Nick | G06Q 10/06 | 700/95 |
| 6,216,109 B1 * | 4/2001 | Zweben | G06Q 10/04 | 705/7.12 |
| 6,253,187 B1 * | 6/2001 | Fox | G06Q 10/087 | 705/28 |
| 6,278,978 B1 * | 8/2001 | Andre | G06Q 10/06 | 705/7.13 |
| 6,574,717 B1 * | 6/2003 | Ngai | G06F 17/30371 | 707/E17.007 |
| 6,681,990 B2 * | 1/2004 | Vogler | G06Q 10/08 | 235/385 |
| 6,843,415 B2 * | 1/2005 | Vogler | G06Q 10/08 | 235/375 |
| 6,845,909 B2 * | 1/2005 | Bong | G06Q 10/087 | 235/375 |
| 6,850,809 B1 * | 2/2005 | Callar | G06Q 10/06 | 700/216 |
| 6,866,195 B2 * | 3/2005 | Knowles | G06Q 10/087 | 235/375 |
| 6,920,427 B2 * | 7/2005 | Anthony | G06Q 10/0631 | 705/28 |
| 7,043,321 B2 * | 5/2006 | Ruml | G05B 19/41865 | 700/100 |
| 7,055,741 B2 * | 6/2006 | Bong | G06Q 10/087 | 235/382 |
| 7,058,587 B1 * | 6/2006 | Horne | G06Q 10/06 | 705/7.22 |
| 7,069,094 B2 | 6/2006 | Kabota et al. | | |
| 7,117,163 B1 * | 10/2006 | Iyer | G06Q 30/02 | 705/7.32 |
| 7,171,376 B2 * | 1/2007 | Ramakrishnan | G06Q 10/04 | 705/14.1 |
| 7,209,869 B1 * | 4/2007 | Kroger | G06Q 10/06 | 703/1 |
| 7,210,624 B1 * | 5/2007 | Birjandi | G06Q 10/00 | 235/385 |
| 7,231,361 B2 * | 6/2007 | Eck | G06Q 10/087 | 705/28 |
| 7,373,371 B2 * | 5/2008 | Eck | G06Q 10/0631 | 705/28 |
| 7,567,917 B2 | 7/2009 | Miller et al. | | |
| 7,664,683 B2 * | 2/2010 | Feldman | G06Q 10/06 | 705/22 |
| 7,778,857 B2 * | 8/2010 | Schierholt | G06Q 10/04 | 705/16 |
| 7,788,070 B2 | 8/2010 | Grichnik et al. | | |
| 2002/0037232 A1 * | 3/2002 | Billiet | B22F 1/0059 | 419/37 |
| 2002/0065764 A1 * | 5/2002 | Brodersen, Jr. | G06Q 10/087 | 705/37 |
| 2002/0095348 A1 * | 7/2002 | Hiroshige | G06Q 10/087 | 705/26.44 |
| 2002/0116281 A1 * | 8/2002 | Costello | G06Q 10/087 | 705/26.3 |
| 2002/0138316 A1 * | 9/2002 | Katz | G06Q 10/06311 | 705/7.13 |
| 2002/0165782 A1 * | 11/2002 | Falkenstein | G06Q 10/0637 | 705/22 |
| 2003/0061088 A1 * | 3/2003 | Sarlay | G06Q 10/04 | 705/7.13 |
| 2003/0105684 A1 * | 6/2003 | Dunn | G06Q 10/087 | 705/28 |
| 2003/0158769 A1 * | 8/2003 | Uno | G06Q 10/06 | 705/7.25 |
| 2004/0024628 A1 * | 2/2004 | Eck | G06Q 10/0631 | 705/29 |
| 2004/0084526 A1 * | 5/2004 | Knowles | G06Q 10/087 | 235/385 |
| 2004/0084527 A1 * | 5/2004 | Bong | G06Q 10/087 | 235/385 |
| 2004/0122689 A1 * | 6/2004 | Dailey | G06Q 10/08 | 705/29 |
| 2004/0158508 A1 * | 8/2004 | Uehara | G06Q 10/087 | 705/28 |
| 2005/0060270 A1 * | 3/2005 | Ramakrishnan | G06Q 10/04 | 705/400 |
| 2005/0103842 A1 * | 5/2005 | Bong | G06Q 10/087 | 235/385 |
| 2005/0177467 A1 * | 8/2005 | Wang | G06Q 10/06315 | 705/28 |
| 2005/0278271 A1 * | 12/2005 | Anthony | G06F 17/50 | 700/107 |
| 2006/0031084 A1 * | 2/2006 | Schierholt | G06Q 10/04 | 705/7.12 |
| 2006/0111874 A1 * | 5/2006 | Curtis | G06Q 10/06 | 702/186 |
| 2006/0206225 A1 * | 9/2006 | Wright | G06F 17/50 | 700/97 |
| 2006/0235555 A1 * | 10/2006 | Seong | G06F 17/5095 | 700/97 |
| 2007/0100881 A1 * | 5/2007 | McDonald | G06Q 10/04 | |
| 2007/0185760 A1 * | 8/2007 | Birjandi | G06Q 10/00 | 705/7.22 |
| 2007/0185786 A1 * | 8/2007 | Ettl | G06Q 10/08 | 705/28 |
| 2007/0282618 A1 * | 12/2007 | Barahona | G06Q 10/04 | 705/338 |
| 2008/0040185 A1 * | 2/2008 | Birjandi | G06Q 10/00 | 703/21 |
| 2008/0120129 A1 * | 5/2008 | Seubert | G06Q 10/06 | 705/35 |
| 2009/0164285 A1 * | 6/2009 | Hurtis | G06Q 10/00 | 705/7.23 |

(56) References Cited

U.S. PATENT DOCUMENTS

2012/0232685 A1* 9/2012 Wang .................. B22D 46/00
                                                  700/98
2014/0188566 A1   7/2014 Pinel et al.
2014/0344013 A1* 11/2014 Karty .................. G06N 3/126
                                                  705/7.29

OTHER PUBLICATIONS

Shahbaz et al., "Product Design and Manufacturing Process Improvement Using Association Rules," Journal of Engineering Manufacture, vol. 220, No. 2, pp. 243-254, Feb. 2006.
Tan et al., "Selecting the Right Interestingness Measure for Association Patterns", ACM SIGKDD, Aug. 23, 2002, pp. 32-41.

* cited by examiner

ASSOCIATION-BASED PRODUCT DESIGN

FIELD OF THE DISCLOSURE

This disclosure relates generally to the field of product design, and relates more specifically to the mining of associations to inspire new products.

BACKGROUND OF THE DISCLOSURE

Product design is the process of creating a new product (i.e., an item that can be offered to a market to satisfy a want or need) to be sold by a business to its customers. Thus, product design broadly involves the generation and development of ideas through a process that leads to new products. The new products may be designed to respond to a stated design objective (e.g., desired feature or intended use) and/or "seed" (e.g., constraint or inspirational starting point).

Conventionally, product design is a human-driven process. That is, the process relies on human product designers to conceptualize and evaluate ideas and turn them into tangible products. Although tools have been developed to relieve product designers of some of these tasks, there are no known tools that can autonomously generate ideas for new products without human assistance.

SUMMARY OF THE DISCLOSURE

A method for designing a new product includes automatically identifying a plurality of components of stored products, wherein the plurality of components is associated with an existing component included in a design of the new product, automatically selecting a new component from among the plurality of components, wherein an association between the existing component and the new component optimizes a design objective for the new product, automatically adding the new component to the design for the new product, and iteratively repeating the identifying, the selecting, and the adding until a stopping criterion is met, wherein the design for the new product is complete when the stopping criterion is met.

In another embodiment, a device for designing a new product includes a processor and a computer-readable medium storing instructions which, when executed by the processor, cause the processor to perform operations including: automatically identifying a plurality of components of stored products, wherein the plurality of components is associated with an existing component included in a design of the new product, automatically selecting a new component from among the plurality of components, wherein an association between the existing component and the new component optimizes a design objective for the new product, automatically adding the new component to the design for the new product, and iteratively repeating the identifying, the selecting, and the adding until a stopping criterion is met, wherein the design for the new product is complete when the stopping criterion is met.

In another embodiment, a system for designing a new product includes a database storing designs for a plurality of stored products, wherein each of the designs for the plurality of stored products comprises a plurality of components, and an application server for iteratively selecting a new component from among the plurality of components, wherein an association between an existing component of a design for the new product and the new component optimizes a design objective for the new product, and for adding the new component to the design for the new product.

BRIEF DESCRIPTION OF THE DRAWINGS

The teachings of the present disclosure can be readily understood by considering the following detailed description in conjunction with the accompanying drawings, in which.

DETAILED DESCRIPTION

Figure 1:
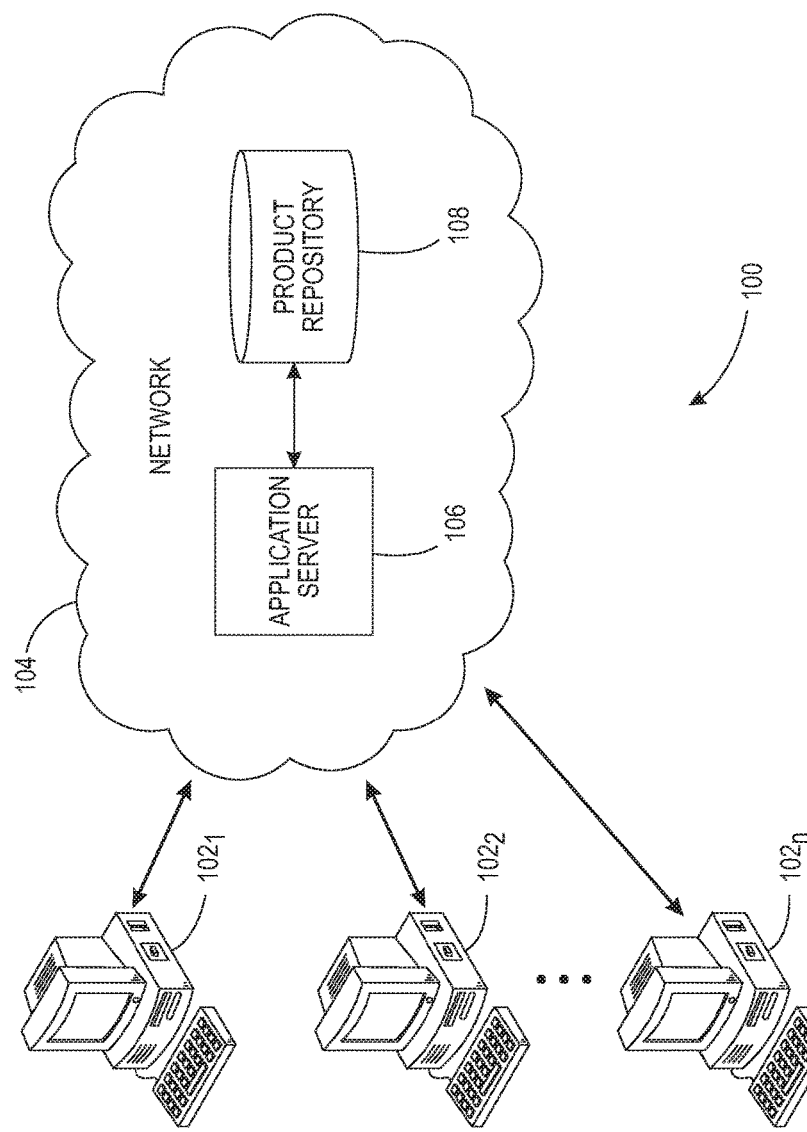
FIG. 1 illustrates one embodiment of a system for designing a product, according to the present disclosure.

In one embodiment, the present disclosure is related to a method and apparatus for association-based product design. At a high level, embodiments of the present disclosure automatically mine data in repositories that store information relating to items and their relationships. Items may be connected to other items for many possible reasons via many possible relationships. For instance, relationships may be domain-specific (e.g., co-occurrence of items in products, products grown in the same season, products with similar functions, products related to similar topics, or products with similar chemical compositions). Data mining leads to the automatic identification of significant associations, which may be characterized by optimization criteria (e.g., interestingness, support for association in mined data, confidence in appropriateness of association, conviction in appropriateness of association, information gain, least contradiction, lift, etc.).

Items that are associated with each other and that optimize some design objective may be automatically combined as components of a new product. The new product could be, for example, a recipe (e.g., where the components include ingredients), a travel itinerary (e.g., where the components include tourist attractions), an electronic device (e.g., where the components include electronic components such as sensors, transceivers, etc.), an architectural blueprint (e.g., where the components include architectural features), a web application (e.g., where the components include software components), a business plan (e.g., where the components include business goals), or an urban plan (e.g., where the components include infrastructure features). Various products can be quickly designed through a flexible process that allows design objectives and/or seeds to be modified dynamically.

Human feedback and evaluation can be naturally integrated into embodiments of the design process. Though not required, human feedback can result in the design of more desired products and can also help the machine system better understand the repositories (which will result in deeper understanding and knowledge of the product design process).

Within the context of the present invention, an "association" refers to a relationship between two or more components that renders those components correlated with or statistically dependent upon each other. More simply put, two or more components may be said to be "associated with" each other if they tend to co-occur in a given context. As discussed above, an association may be imputed by many different types of relationships, which may be domain-specific.

Embodiments of the present disclosure can thus be used to improve the efficiency and reduce the complexity of the product design process by reducing the required amount of human effort. The present disclosure may also be capable of achieving a better balance of traditional design patterns and computational creativity. For instance, the present disclosure can be employed to explore user habits (e.g., from mining the repositories) and guide new usage trends (e.g., by leveraging new design objectives and seeds).

Embodiments of the above-described product design process are performed entirely by machine systems, with little or no assistance from a human product designer. For instance, a machine system may identify item associations and conceptualize a new product based on those associations, but may optionally solicit human feedback regarding the resultant new product.

One aspect of the present disclosure is to modify a function of a computer based on receipt of human feedback. For instance, as discussed above, a human product designer or supervisor may provide feedback regarding a new product that has been designed by a machine system, which may include one or more computers. This feedback may be used by the machine system to inform the design of subsequent products. Notably, a machine is required to modify certain portions of the computer as product designs are evaluated and/or modified.

Embodiments of the present disclosure identify sets of related items (e.g., food ingredients, tourist attractions, architectural features, etc.) that optimize a defined objective and then transform the sets of related items into suggested new products that meet the defined objective. In other words, the items alone do not typically dictate how or whether they can be combined. However, embodiments of the present disclosure select disparate items and transform them into suggested products that comprise some composite of the disparate items.

In addition, because of the transformation of the information, the functioning of the computer and/or machine system is improved. For example, the functioning of the computer is greatly improved by providing a method that modifies the operation of the computer based on product feedback received from a human supervisor. Notably, previous computers were incapable of modifying their functionality based on feedback regarding new products designed by the computers. Therefore, the functioning of the computer is clearly improved.

FIG. 1 illustrates one embodiment of a system 100 for designing a product, according to the present disclosure. The system 100 generally comprises one or more endpoint devices $102_1$-$102_n$ (hereinafter collectively referred to as endpoint devices 102") coupled to a network 104. The network 104, in turn, generally comprises an application server 106 and one or more databases $108_1$-$108_m$ (hereinafter collectively referred to as "databases 108").

The network 104 is a communications network. The network 104 may be any type of communications network, such as for example, a traditional circuit switched network (e.g., a public switched telephone network (PSTN)) or an Internet Protocol (IP) network (e.g., an IP Multimedia Subsystem (IMS) network, an asynchronous transfer mode (ATM) network, a wireless network, a cellular network (e.g., 2G, 3G and the like), a long term evolution (LTE) network, and the like) related to the current disclosure. It should be noted that an IP network is broadly defined as a network that uses Internet Protocol to exchange data packets. Additional exemplary IP networks include Voice over IP (VoIP) networks, Service over IP (SoIP) networks, and the like.

In one embodiment, the network 104 may comprise a core network that is in communication with one or more access networks (not shown), where the access networks may include a wireless access network (e.g., a WiFi network and the like), a cellular access network, a PSTN access network, a cable access network, a wired access network and the like. In one embodiment, the access networks may all be different types of access networks, may all be the same type of access network, or some access networks may be the same type of access network and other may be different types of access networks. The core network and the access networks may be operated by different service providers, the same service provider or a combination thereof.

As discussed above, the network 104 includes an application server 106 and one or more databases 108. Although only a single application server 106 and a single 108 are illustrated, it should be noted that any number of application servers 106 or databases 108 may be deployed.

Figure 6:
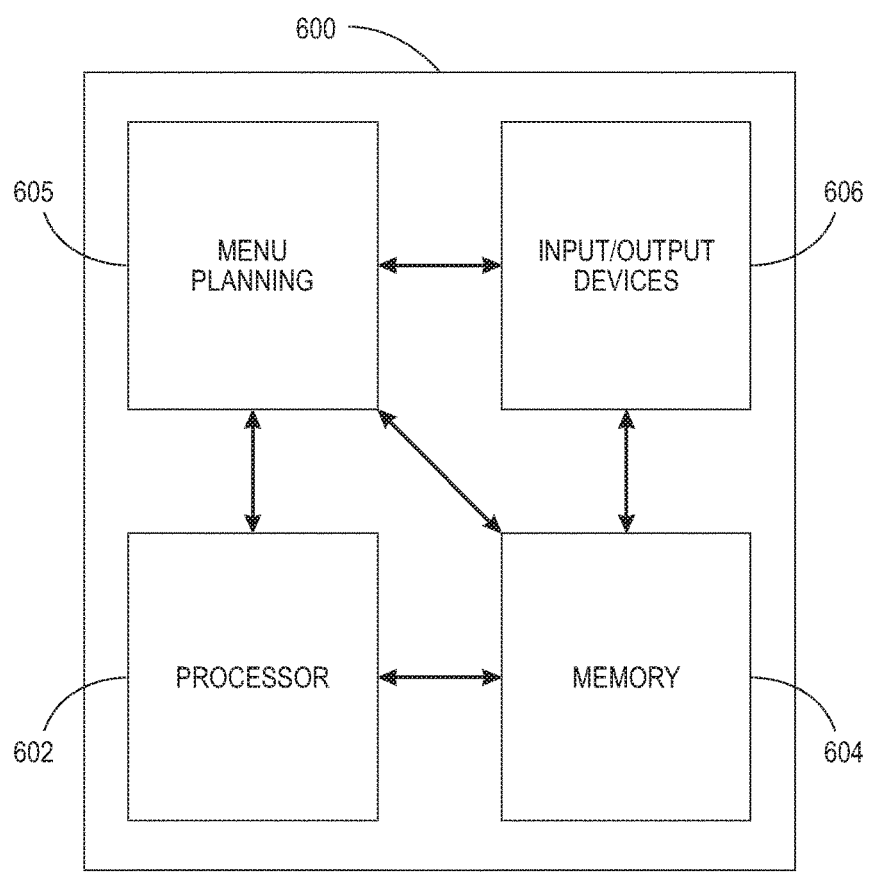
FIG. 6 is a high-level block diagram of a general purpose computing device suitable for use in performing the functions described herein.

One embodiment of an application server 106 is described in greater detail in connection with FIG. 2. In another embodiment, the application server 106 may comprise a general purpose computer configured as a special purpose computer, as illustrated in FIG. 6 and discussed below. In one embodiment, the application server 106 may perform the methods and algorithms discussed below related to designing a new product. For instance, the application server 106 may mine a repository of existing products for associations between components, and employ those associations to design new products comprising new combinations of components.

In one embodiment, the database 108 may store data relating to existing product designs. Thus, the database 108 illustrated in FIG. 1 is a product repository. This data can be supplemented with data relating to new product designs, as the new products designs are developed, evaluated, and finalized. In an alternative embodiment, multiple databases 108 may store the data.

In one embodiment, the network 104 is in communication with the endpoint devices 102. In one embodiment, the endpoint devices 102 may be any type of computing device such as a desktop computer, a tablet computer, a laptop computer, a netbook, an ultrabook, a cellular telephone, a smart phone, a portable media device (e.g., an MP3 player), a gaming console, a portable gaming device, and the like. It should be noted that although only three endpoint devices 102 are illustrated in FIG. 1, any number of endpoint devices 102 may be deployed.

In an alternative embodiment, the methods performed by the application server 106 may be performed locally by the endpoint devices 102. In this case, the endpoint devices 102 access the databases 108 directly over the network 104 and perform the methods and algorithms discussed below related to designing a product.

It should be noted that the network 104 has been simplified. For example, the network 104 may include other network elements (not shown) such as border elements, routers, switches, policy servers, security devices, a content distribution network (CDN) and the like.

Figure 2:
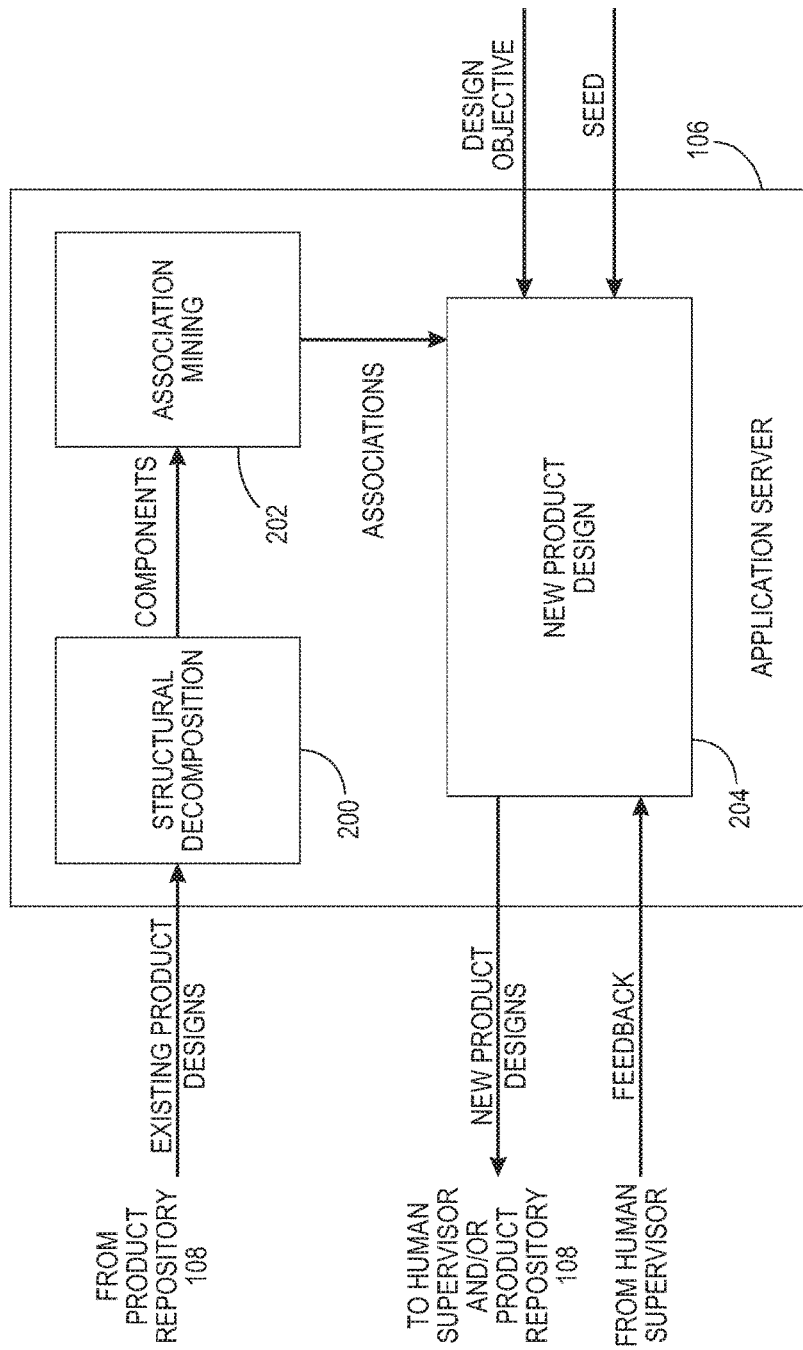
FIG. 2 is a block diagram illustrating the application server of FIG. 1 in greater detail.

FIG. 2 is a block diagram illustrating the application server 106 of FIG. 1 in greater detail. In general, the application server 106 receives a plurality of inputs, from the product repository 108 and/or from endpoint devices 102. The plurality of inputs relates to existing product designs, as well as to design objectives, seeds, and/or feedback for new product designs. The application server 106 produces as output a new product design, which may be responsive to at least some of the plurality of inputs. Thus, the application server 106 according to embodiments of the present disclosure transforms a set of data (e.g., individual components) into a suggested new product design (e.g., a design for a new product that incorporates at least some of the individual components and optionally meets a stated design objective).

The application server 106 generally comprises a structural decomposition engine 200, an association mining engine 202, and a new product design engine 204. Any of the structural decomposition engine 200, the association mining engine 202, and the new product design engine 204 may be implemented as a processor.

The structural decomposition engine 200 obtains existing (stored) product designs, for example from the database 108, and decomposes the designs into component parts. The products designs may be decomposed with varying degrees of modularity (e.g., anywhere from individual component-level to sub-assemblies comprising multiple, but less then all, of the components). Finding the right degree of modularity involves a tradeoff between flexibility and coherence and may include determining relationships between components.

The association mining engine 202 obtains the components from the structural decomposition engine 200 and examines the components for associations (i.e., interesting patterns in the relationships between components).

The new product design engine 204 obtains the associations from the association mining engine 202. Moreover, the new product design engine 204 obtains as additional inputs a "seed" for inspiration and one or more design objectives. The seed may be, for example, x. The design objectives might include, for example, novelty, quality, balance, or cost. The new product design engine 204 designs a suggested new product, responsive to these various inputs. In one embodiment, design of the suggested new product is an iterative process in which the new product design engine 204 iteratively adds new components that are associated with existing components in interesting ways. In addition, the new product design engine 204 may optimize the design of the suggested new product. Thus, the new product design engine 204 evaluates combinations of seeds and associated components in order to determine how well the combinations meet stated design objectives, and then chooses optimal combinations as suggested new product designs.

The new product design engine 204 may output the design of the suggested new product for review and/or storage. For instance, a human supervisor may review the design of the suggested new product and provide feedback on the design. This feedback may be considered by the new product design engine 204 as an additional input and may motivate modification of the suggested new product design. Alternatively or in addition, the suggested new product design may be saved in the database 108 for future use (e.g., in designing additional new products).

Figure 3:
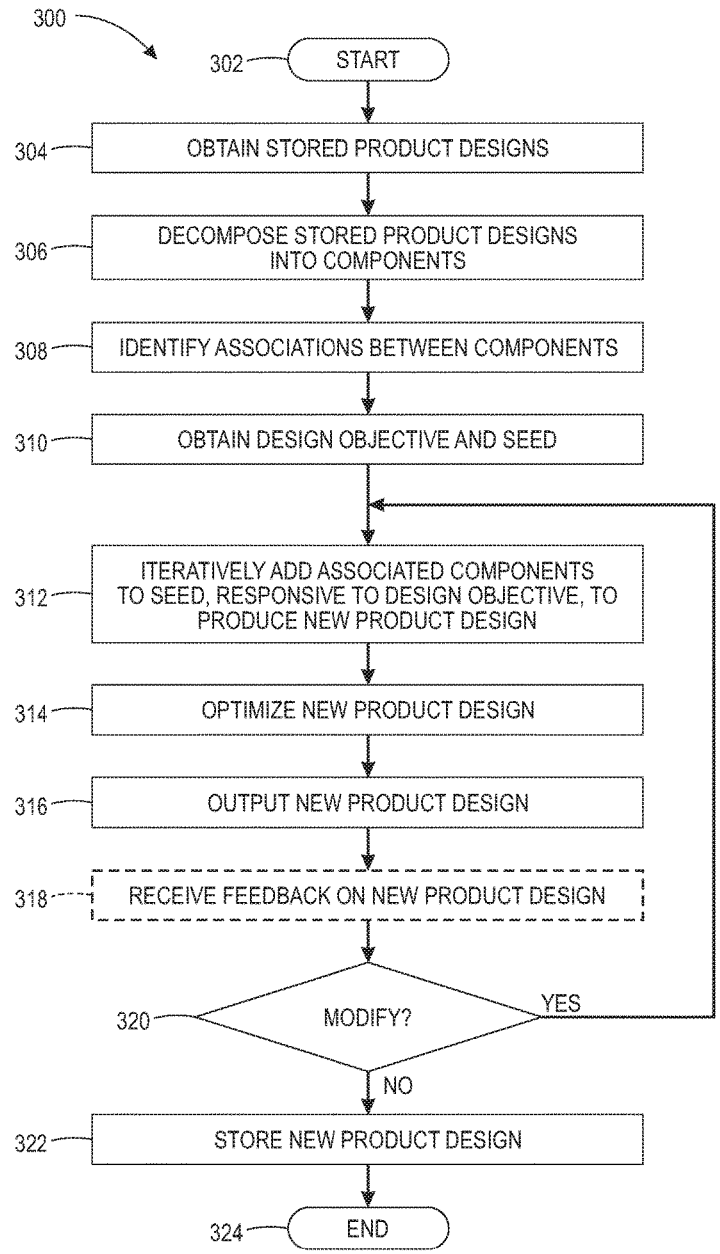
FIG. 3 is a flow diagram illustrating the high level method for designing a product, according to embodiments of the present disclosure.

FIG. 3 is a flow diagram illustrating the high level method 300 for designing a product, according to embodiments of the present disclosure. The method 300 may be performed, for example, by the application server 106 illustrated in FIGS. 1 and 2 and described in detail above. However, it will be appreciated that the method 300 is not limited to implementation on the application server 106; in alternate embodiments, the method 300 may be performed by other devices or systems, including the endpoint devices 102 or a general purpose computing device that is configured as a special purpose computing device.

Figure 4:
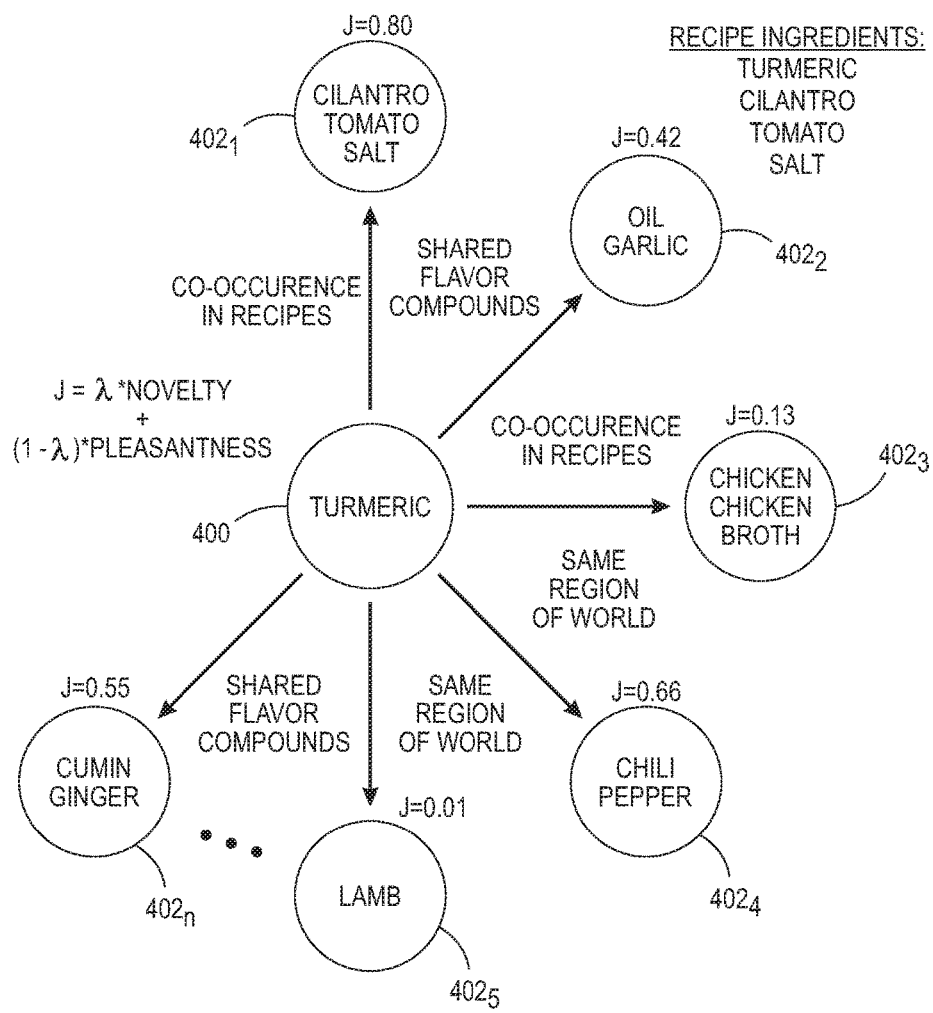
FIG. 4 depicts a conceptual illustration of part of the process for designing a new product.

As an example, the method 300 assumes that a new product to be designed is a recipe, where the "components" of the new product are ingredients or combinations of ingredients. This example will be used for illustrative purposes to provide better understanding of the steps of the disclosed process. FIG. 4, for example, depicts a conceptual illustration of part of the process for designing a new product (i.e., a recipe). It will be understood that this example does not limit the disclosed process in any way. For instance, the new product could just as easily be a travel itinerary (e.g., where the components include tourist attractions), an electronic device (e.g., where the components include electronic components such as sensors, transceivers, etc.), an architectural blueprint (e.g., where the components include architectural features), a web application (e.g., where the components include software components), a business plan (e.g., where the components include business goals), or an urban plan (e.g., where the components include infrastructure features).

The method 300 begins in step 302. In step 304, the structural decomposition engine 200 obtains stored product designs, for example from the database 108. Where the new product to be designed is a recipe, the stored product designs may include stored recipes.

In step 306, the structural decomposition engine 200 decomposes the stored product designs into components. As discussed above, the stored product designs may be decomposed with varying degrees of granularity (e.g., anywhere from individual component-level to sub-assemblies comprising multiple, but less than all, of the components in a design). Where the stored product designs are recipes, for example, components may comprise single ingredients (e.g., lamb) or combinations of ingredients (e.g., cilantro, tomato, and salt). For example, FIG. 4 illustrates a plurality of components $402_1$-$402_n$ (hereinafter "components 402") that may be derived by the structural decomposition engine 200 from stored recipes.

In step 308, the association mining engine 202 identifies associations between components. The associations comprise interesting patterns in the relationships between components. For example, where the components are ingredients of recipes, relevant associations might include co-occurrence of components in recipes, components with shared flavor compounds, components obtained from the same regions of the world (i.e., same region of origin), or components that are grown in the same season of the year. To improve efficiency, only those associations that are considered to be interesting are reported, where the "interestingness" of an association refers to how dependent associated component are on each other. The interestingness of an association may be measured mathematically in any one of a variety of ways, and the selection of a specific mathematical formulation may be dependent upon the domain under consideration (e.g., recipes versus travel versus electronic devices, etc.). Some specific examples of metrics that have been used to evaluate the interestingness of associations include support, confidence, lift, correlation, and collective strength, among other measures.

In step 310, the new product design engine 204 obtains a design objective and a seed. In one embodiment, the seed is a starting component for the new product to be designed.

Where the new product is a recipe, for example, the seed may be an ingredient that is required to be included in the recipe. For example, FIG. 4 illustrates a single seed 400 (e.g., turmeric) that may be obtained as the starting point for designing a new recipe. A new product may start with more than one seed. The design objective is a desired feature or intended use for the new product to be designed. For example, where the new product is a recipe, a design objective might be to produce a recipe that is perceived to be novel and pleasant tasting. A new product may be designed to meet more than one design objective. Where there are multiple design objectives, the multiple design objectives may be balanced in a number of ways (for example by assigning weights to the objectives, as discussed in greater detail below.

In step 312, the new product design engine 204 iteratively adds components to the seed. This step may be considered coincident with the step 314 of optimizing the new product design, as discussed in further detail below. The added components are components that are determined to be associated with the seed, according to the associations identified by the association mining engine 202. For example, FIG. 4 illustrates several different components 402 that are determined to be associated with the seed 400, based on different types of relationships. For instance, the combination of tomato, cilantro, and salt occurs in some of the same recipes as turmeric. The combination of oil and garlic shares flavor compounds with turmeric. Chile peppers are grown in the same region of the world as turmeric. In one embodiment, components are evaluated for addition based on how interesting the association is in light of the design objective. That is, a goal is to maximize the design objective by adding the optimal components. For instance, if the new product is a recipe and the design objectives are to produce a recipe that is perceived to be both novel and pleasant tasting, the design objective J may be quantified as $J=\lambda^*novelty+(1-\lambda)^*pleasantness$, where $\lambda$, is a variable weight that balances the design objectives of novelty and pleasantness. FIG. 4 illustrates exemplary scores for the various components 402 using this formulation. It is noted that this formulation represents only one way in which multiple design objectives may be balanced in a quantifiable manner.

Figure 5:
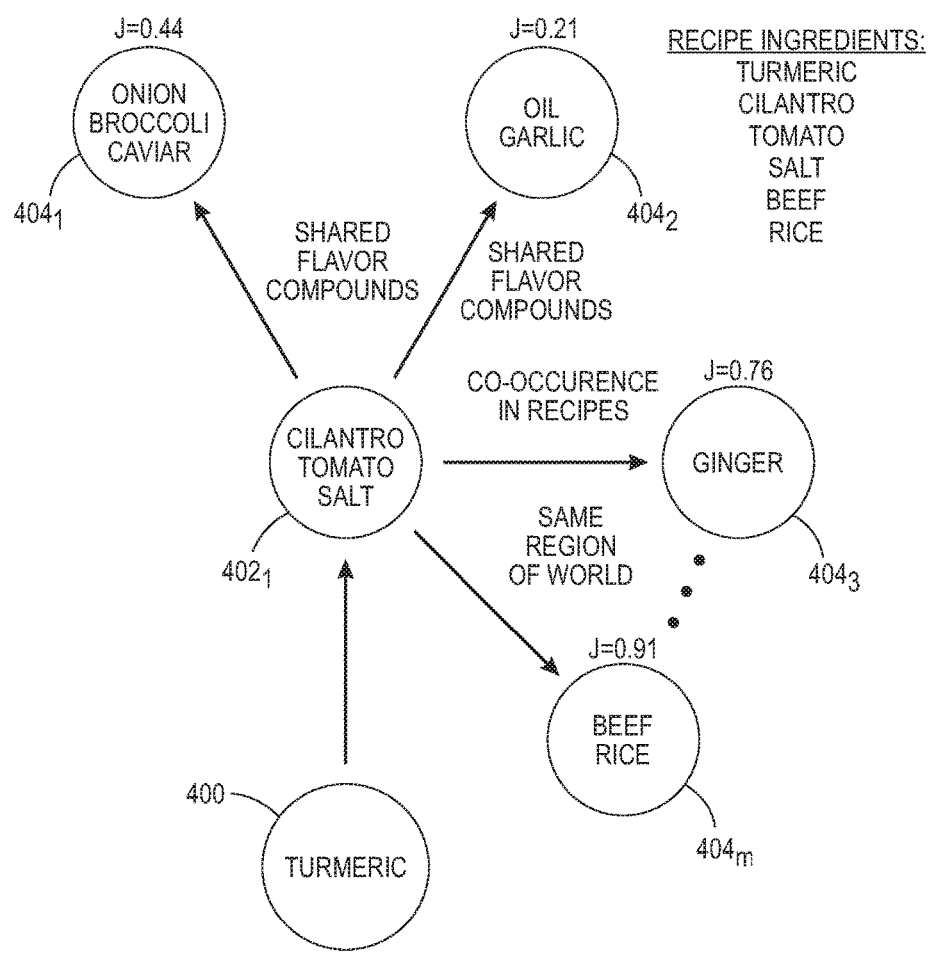
FIG. 5 depicts a conceptual illustration of a further part of the process for designing a new product.

As discussed above, step 312 (and 314) is an iterative process. That is, components are added to the new product iteratively by traversing interesting associations, while also maximizing the design objective. For instance, referring again to FIG. 4, the component $402_1$ has the highest score, J, out of all of the components. Thus, the component $402_1$ can be considered to maximize the design objectives when considered against all of the other potential components 402 that may be added at this stage. Thus, cilantro, tomato, and salt are added to the recipe, which also includes turmeric. Next, the associations are searched for components that are associated with the combination of cilantro, tomato, and salt. FIG. 5, for example, depicts a conceptual illustration of a further part of the process for designing a new product (i.e., a recipe). The components $404_1$-$404_m$ (hereinafter "components 404") are evaluated for how well they meet the design objectives of novelty and pleasantness when added to the combination of cilantro, tomato, and salt. In this case, component $404_m$ can be considered to maximize the design objectives when considered against all of the other potential components 404 that may be added at this stage. Thus, beef and rice are added to the recipe, which also includes cilantro, tomato, salt, and turmeric.

The iterations may continue until some sort of stopping criterion is met. The stopping criterion may be some quantitative measure of how well the design objective has been met. Alternatively, the stopping criterion may be some threshold number of iterations that are performed without an improvement in the quantitative measure. The stopping criterion could alternatively be a threshold number of iterations. Other stopping criteria are also possible. Once the stopping criterion has been met, the result of the iterative process is a complete new product composed of a plurality of components.

Once the stopping criterion has been met, the method 300 proceeds to step 316, where the new product design engine 204 outputs the new product design. The new product design may be output, for example, to an endpoint device 102, where it can be reviewed by a human supervisor. Alternatively, the new product design may be output to the database 108 for storage.

In optional step 318 (illustrated in phantom), the new product design engine 204 receives feedback on the new product design from a human supervisor. In step 320, the new product design engine 204 determines whether to modify the new product design in response to the feedback.

If the new product design engine 204 concludes in step 320 that the new product design should be modified, then the method 300 returns to step 312 and proceeds as described above to modify the new product design (e.g., using associations between components). Alternatively, if the new product design engine 204 concludes in step 320 that the new product design should not be modified, then the new product design is stored (e.g., in the database 108) in step 322.

The method 300 ends in step 324.

FIG. 6 depicts a high-level block diagram of a general-purpose computer suitable for use in performing the functions described herein. As depicted in FIG. 6, the system 600 comprises a hardware processor element 602 (e.g., a central processing unit (CPU), a microprocessor, or a multi-core processor), a memory 604, e.g., random access memory (RAM) and/or read only memory (ROM), a module 605 for designing a new product, and various input/output devices 606 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the respective systems and/or methods discussed above can be used to configure a hardware processor to perform the steps functions and/or operations of the above disclosed systems and methods. In one embodiment, instructions and data for the present module or process 605 for designing a new product (e.g., a software program comprising computer-executable instructions) can be loaded into memory 604 and executed by hardware processor element 602 to implement the steps, functions or operations as discussed above in connection with the exemplary systems 100 and 106 and/or method 300. The processor executing the computer readable or software instructions relating to the above described method(s) can be perceived as a programmed processor or a specialized processor. As such, the present module 605 for designing a new product (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

Referring to FIG. 6, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A non-transitory computer-readable medium storing instructions which, when executed by a processor, cause the processor to perform a method for designing a new product, the method comprising:
   automatically identifying, by a processor, a plurality of components of stored products, wherein the plurality of components is associated with an existing component included in a design of the new product;
   automatically selecting, by the processor, a new component from among the plurality of components, wherein an association between the existing component and the new component optimizes a design objective for the new product;
   automatically adding, by the processor, the new component to the design for the new product, wherein a result of the automatically adding is a complete design for the new product;
   receiving, by the processor, human feedback relating to the complete design for the new product; and
   repeating, by the processor, at least one of the automatically identifying, the automatically selecting, or the automatically adding, in response to the human feedback, in order to modify the complete design.

2. The non-transitory computer-readable medium of claim 1, wherein the automatically identifying, the automatically selecting, and the automatically adding are performed without human assistance.

3. The non-transitory computer-readable medium of claim 1, wherein the association is domain-specific.

4. The non-transitory computer-readable medium of claim 1, wherein the association is a co-occurrence of the existing component and the new component in the stored products.

5. The non-transitory computer-readable medium of claim 1, wherein the association is a function shared by the existing component and the new component.

6. The non-transitory computer-readable medium of claim 1, wherein the association is a chemical composition shared by the existing component and the new component.

7. The non-transitory computer-readable medium of claim 1, wherein the association is a seasonal availability shared by the existing component and the new component.

8. The non-transitory computer-readable medium of claim 1, wherein the association is a region of origin shared by the existing component and the new component.

9. The non-transitory computer-readable medium of claim 1, wherein the automatically identifying comprises:
   automatically obtaining, by the processor, designs for the stored products from a repository;
   decomposing the designs for the stored products into the plurality of components; and
   detecting that the plurality of components is related to the existing component.

10. The non-transitory computer-readable medium of claim 9, wherein the plurality of components includes individual components.

11. The non-transitory computer-readable medium of claim 9, wherein the plurality of components includes sub-assemblies comprising multiple individual components.

12. The non-transitory computer-readable medium of claim 1, wherein the automatically selecting comprises:
   generating, by the processor, for each of the plurality of components, a quantitative measure of how well an association between the each of the plurality of components and the existing component satisfies the design objective, wherein the quantitative measure associated with the new component is highest among quantitative measures for the plurality of components.

13. The non-transitory computer-readable medium of claim 12, wherein the design objective is one of a plurality of design objectives that are balanced by the quantitative measure.

14. The non-transitory computer-readable medium of claim 1, wherein the existing component is a starting component for the design for the new product.

15. The non-transitory computer-readable medium of claim 1, wherein the existing component was added to the design for the new product in a previous iteration of the automatically adding.

16. The non-transitory computer-readable medium of claim 1, wherein the method further comprises:
   storing the design for the new product when the design for the new product is complete.

17. The non-transitory computer-readable medium of claim 1, wherein the association between the existing component and the new component is observed through data mining.

18. The non-transitory computer-readable medium of claim 1, further comprising:
   prior to receiving the human feedback, iteratively repeating the identifying, the selecting, and the adding until no improvement in a quantitative measure of how well the design for the new product meets the design objective is observed for a threshold number of iterations of the identifying, the selecting, and the adding.

19. The non-transitory computer-readable medium of claim 1, further comprising:
   prior to receiving the human feedback, iteratively repeating the identifying, the selecting, and the adding until a value of a quantitative measure of how well the design for the new product meets the design objective meets a target value.

20. The non-transitory computer-readable medium of claim 1, further comprising:

prior to receiving the human feedback, iteratively repeating the identifying, the selecting, and the adding until the iteratively repeating is performed a threshold number of times.

* * * * *